US009662142B2

(12) United States Patent
Roberto et al.

(10) Patent No.: US 9,662,142 B2
(45) Date of Patent: May 30, 2017

(54) METHOD AND DEVICE FOR RESTABILIZATION WITH AXIAL ROTATION OF THE ATLANTOAXIAL JUNCTION

(71) Applicant: Cervical Solutions, LLC, Corvallis, OR (US)

(72) Inventors: Rolando Roberto, Sacramento, CA (US); Kristen Lipscomb, Corvallis, OR (US); Enoch Leung, Southfield, OR (US); Roberto Barragan, Sacramento, CA (US)

(73) Assignee: Cervical Solutions, LLC, Corvallis, OR (US)

( * ) Notice: Subject to any disclaimer, the term of this patent is extended or adjusted under 35 U.S.C. 154(b) by 0 days.

(21) Appl. No.: 14/550,161

(22) Filed: Nov. 21, 2014

(65) Prior Publication Data
US 2015/0209084 A1     Jul. 30, 2015

Related U.S. Application Data

(63) Continuation of application No. PCT/US2013/042280, filed on May 22, 2013.

(60) Provisional application No. 61/650,403, filed on May 22, 2012.

(51) Int. Cl.
*A61B 17/70*     (2006.01)

(52) U.S. Cl.
CPC ...... *A61B 17/7023* (2013.01); *A61B 17/7011* (2013.01); *A61B 17/7034* (2013.01); *A61B 17/7043* (2013.01); *A61B 17/7055* (2013.01); *A61B 17/7067* (2013.01); *A61B 17/7049* (2013.01)

(58) Field of Classification Search
CPC ............ A61B 17/7067; A61B 17/7049; A61B 17/7043
See application file for complete search history.

(56) References Cited

U.S. PATENT DOCUMENTS

| | | | | |
|---|---|---|---|---|
| 5,437,671 A | * | 8/1995 | Lozier | A61B 17/7043 606/252 |
| 7,563,283 B2 | * | 7/2009 | Kwak | A61B 17/7022 606/257 |
| 8,920,471 B2 | * | 12/2014 | Barrus | A61B 17/7052 606/250 |
| 2006/0079896 A1 | * | 4/2006 | Kwak | A61B 17/7023 606/257 |
| 2006/0084991 A1 | | 4/2006 | Borgstrom et al. | |
| 2006/0149229 A1 | * | 7/2006 | Kwak | A61B 17/7023 606/256 |
| 2008/0091200 A1 | | 4/2008 | Kuiper et al. | |
| 2008/0091271 A1 | * | 4/2008 | Bonitati | A61F 2/38 623/20.34 |

(Continued)

OTHER PUBLICATIONS

International Search Report and Written Opinion mailed Sep. 6, 2013, from PCT Application No. PCT/US2013/042280 (10 pages).

(Continued)

*Primary Examiner* — Ellen C Hammond
(74) *Attorney, Agent, or Firm* — Berkeley Law & Technology Group, LLP

(57) ABSTRACT

An apparatus for stabilizing an atlantoaxial junction while allowing for axial rotation in cases of acquired ligamentous injury or fracture of the dens.

8 Claims, 8 Drawing Sheets

(56) References Cited

U.S. PATENT DOCUMENTS

2008/0103501 A1 5/2008 Ralph et al.
2010/0152575 A1 6/2010 Henderson et al.
2011/0022094 A1 1/2011 Ritland

OTHER PUBLICATIONS

International Preliminary Report on Patentability mailed Dec. 4, 2014, from PCT Application No. PCT/US2013/042280 (7 pages).

* cited by examiner

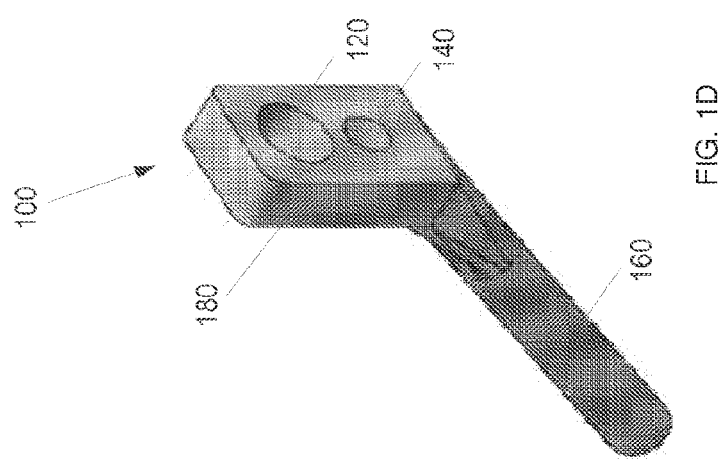
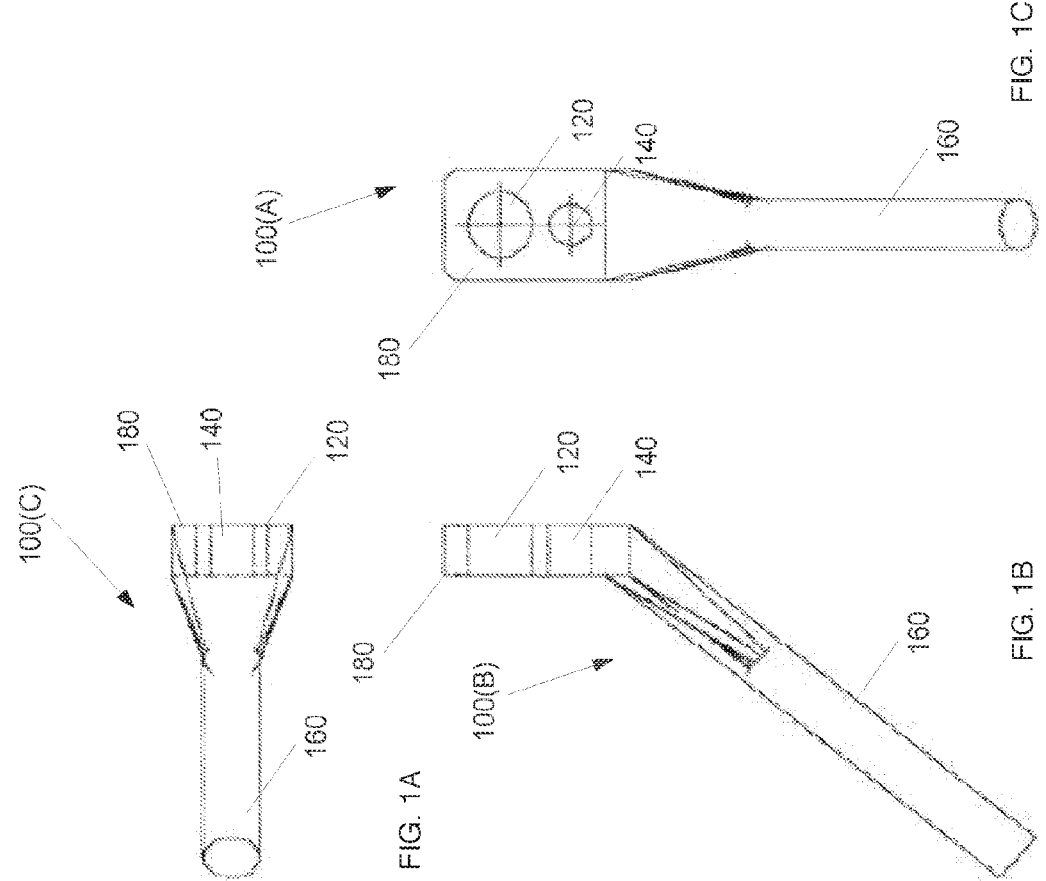

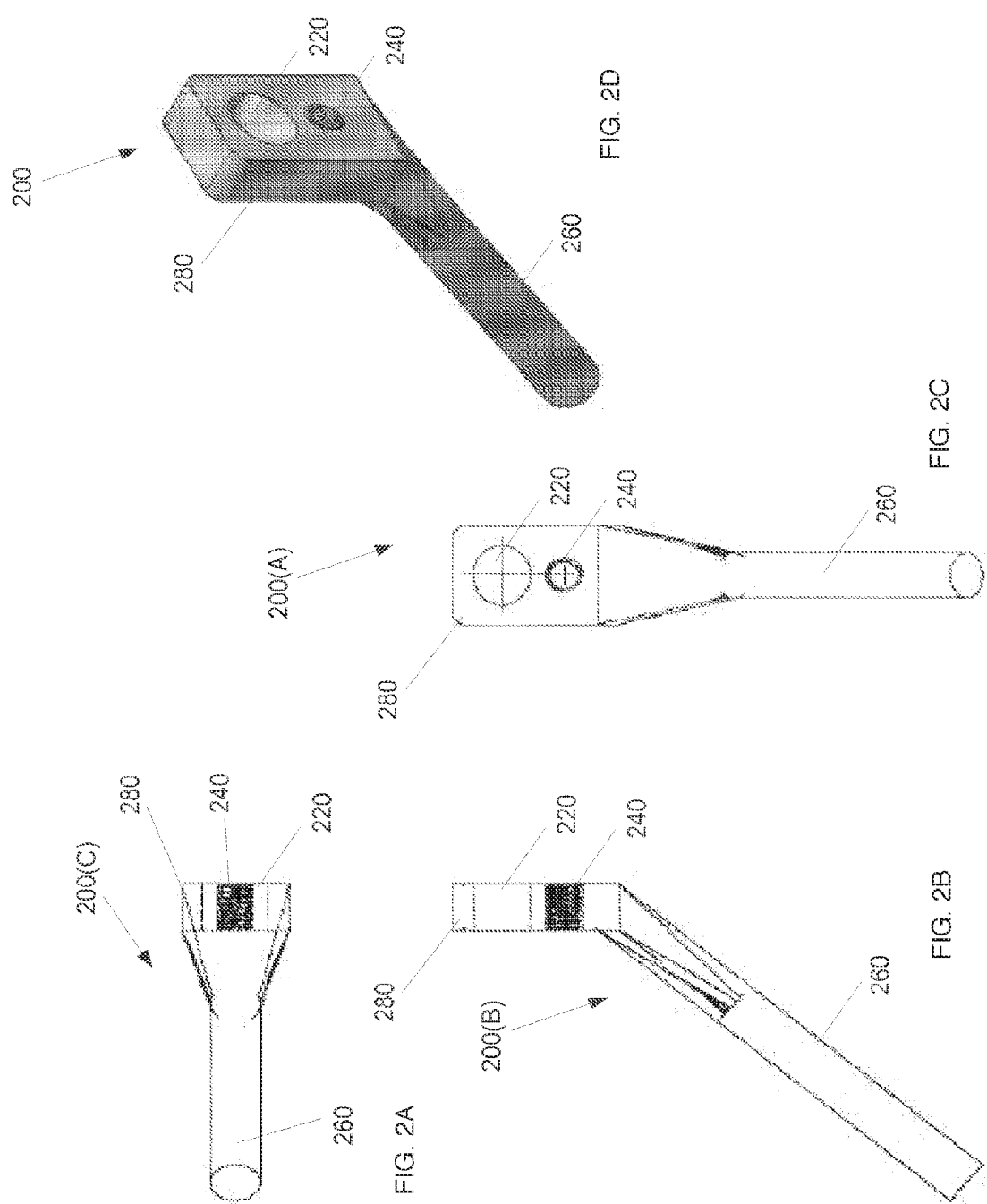

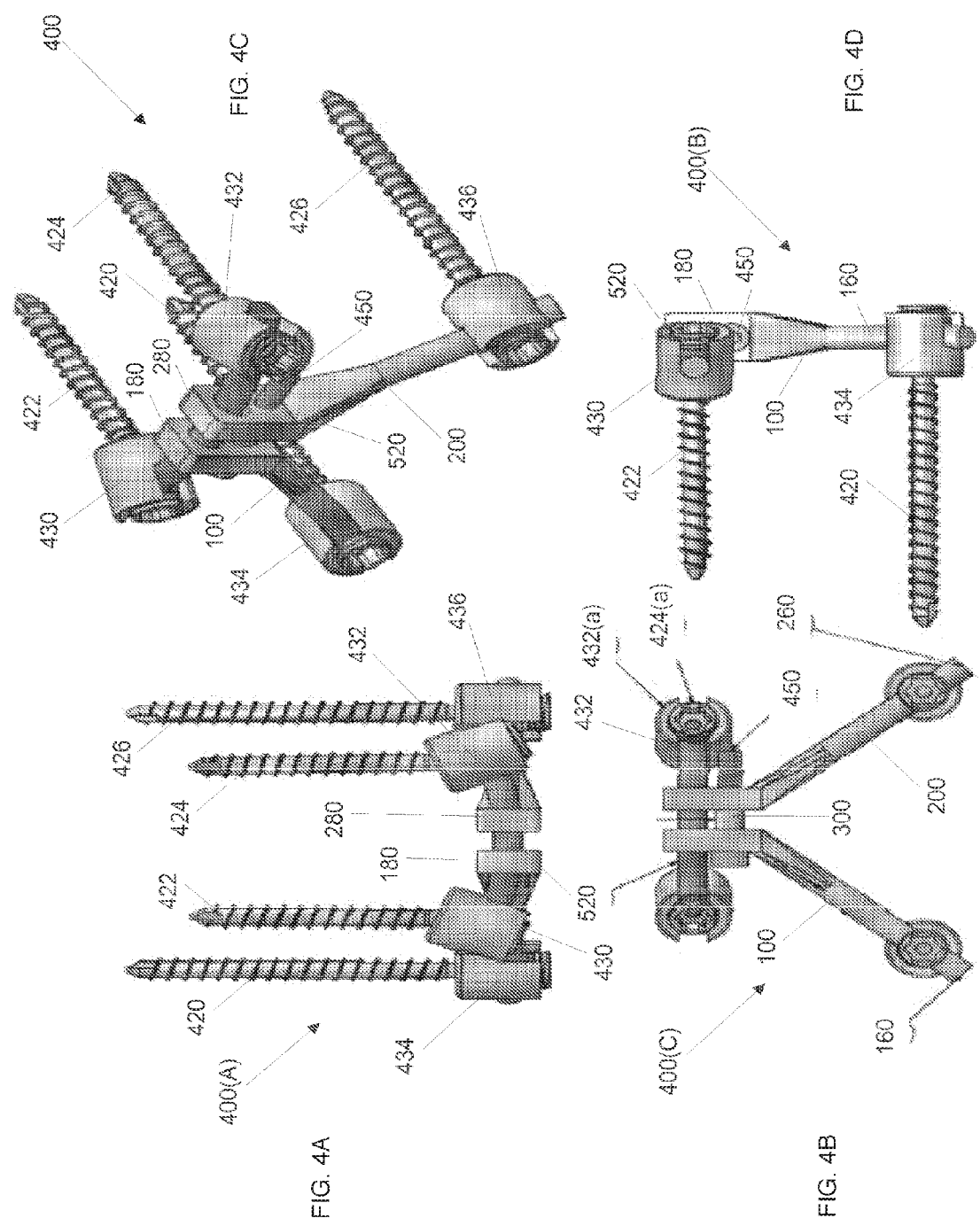

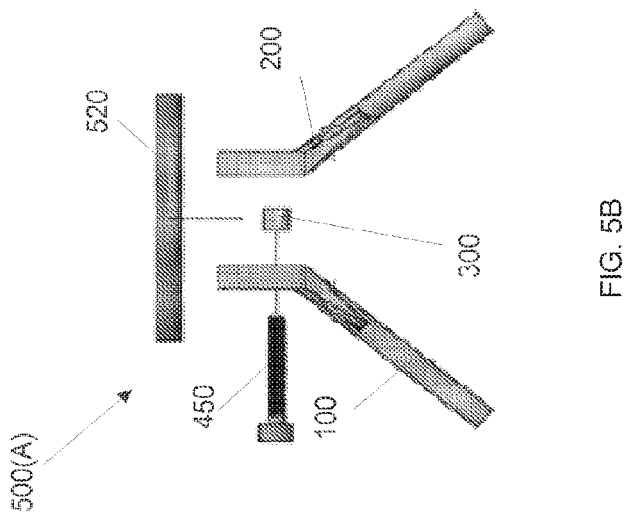
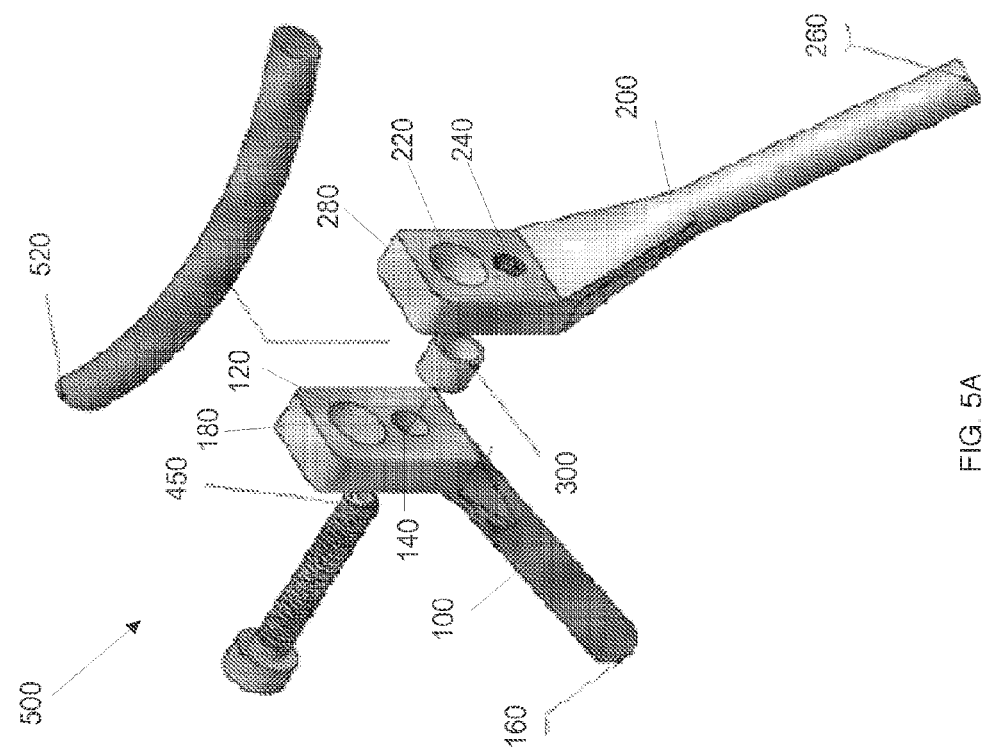

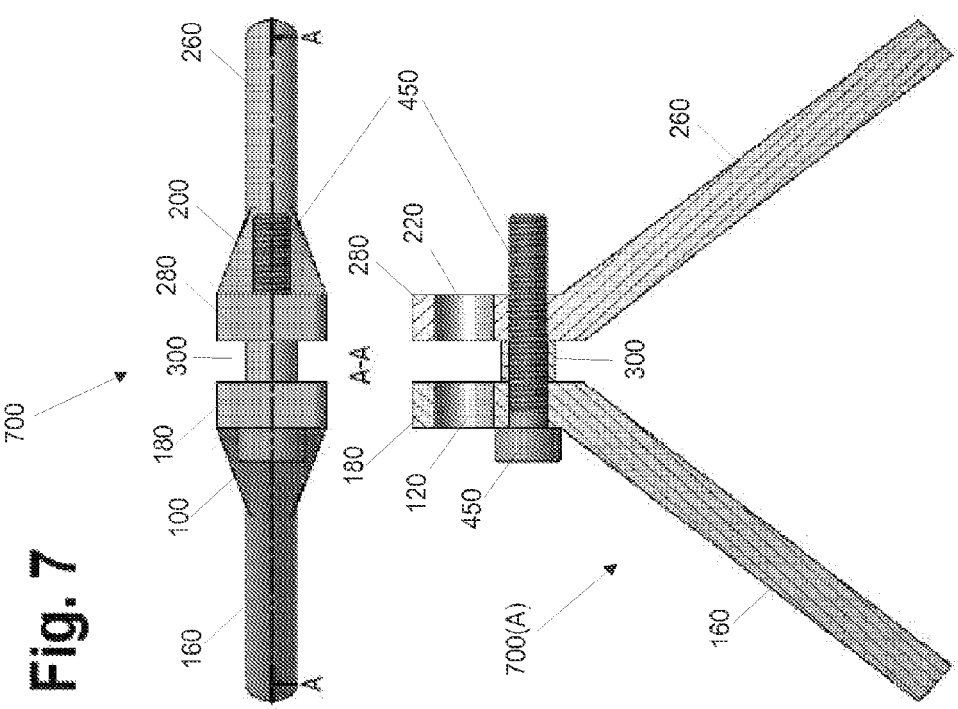

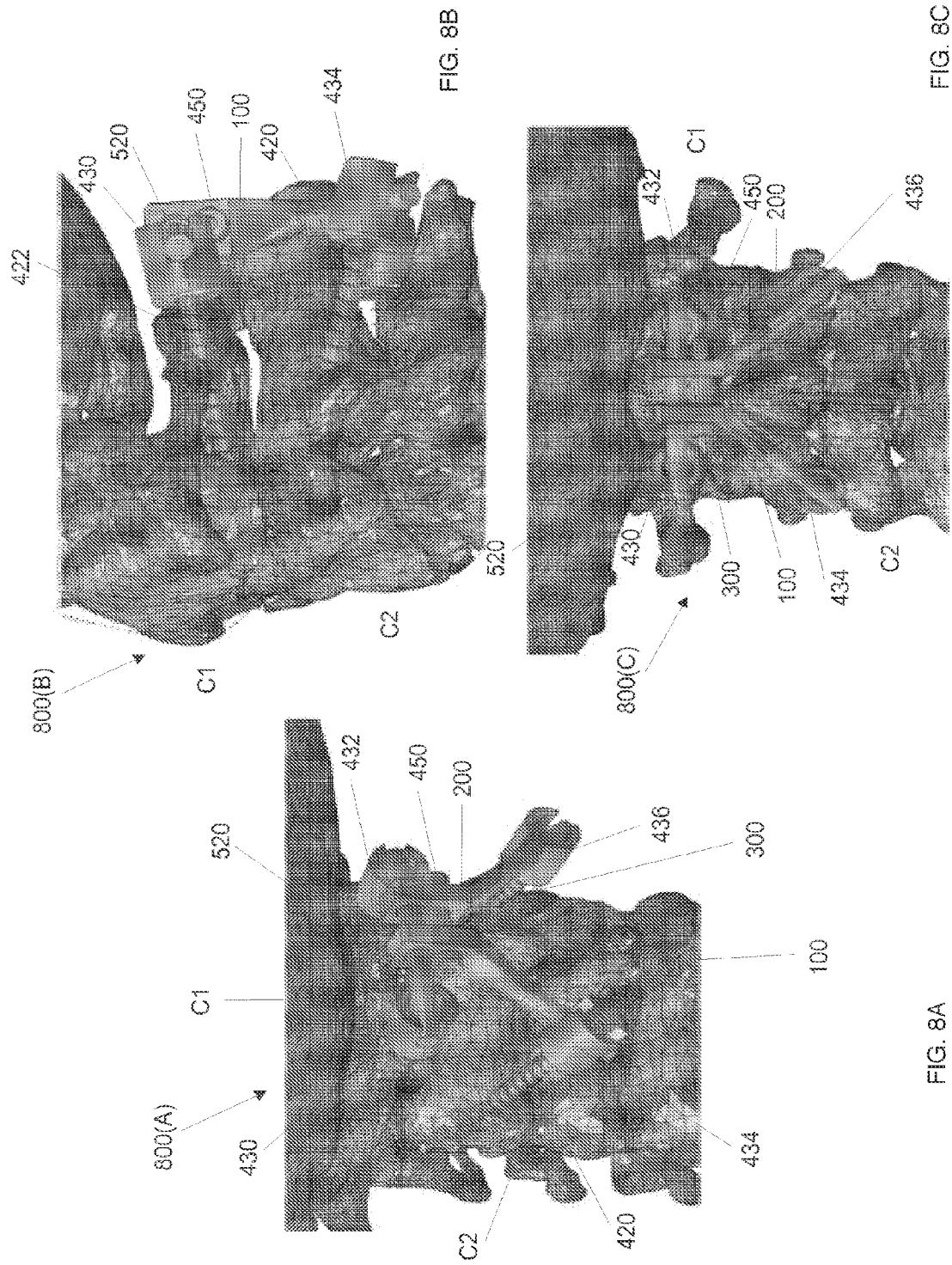

METHOD AND DEVICE FOR RESTABILIZATION WITH AXIAL ROTATION OF THE ATLANTOAXIAL JUNCTION

BACKGROUND OF THE INVENTION

This application is a continuation of International Patent Application No. PCT/US2013/042280, filed on May 22, 2013, which claims the benefit of U.S. Provisional Application No. 61/650,403, filed on May 22, 2012, which are all incorporated by reference herein.

Injuries to the atlanto-axial junction (e.g. odontoid fractures, transverse ligament injuries) are common occurrences, affecting approximately up to 50,000 individuals each year in the United States. Surgical intervention is frequently necessary to prevent atlanto-axial subluxation with concomitant spinal cord injury. To prevent post-injury displacement, spinal fusion (arthrodesis) is performed to fuse the 1st and 2nd cervical vertebrae and thus stabilize the affected area.

Many fixation devices for stabilizing the atlantoaxial junction are configured to completely prevent relative motion. However, arthrodesis limits rotation of the upper cervical spine and head, which can negatively impact an individual's participation in simple activities of daily living. In addition, spinal arthrodesis has been found to increase loading stress at adjacent segments with a potential for acceleration of rates of degeneration.

BRIEF SUMMARY OF THE INVENTION

Embodiments of the invention are related to a method for stabilization of the atlantoaxial junction while allowing for axial rotation in cases of acquired ligamentous injury or fracture of the dens. In the method, an orthopedic device can be implanted using standard spine screws. The orthopedic device includes a curved guide rod and a modular device. The guide rod can be secured to the lateral masses of the 1st cervical vertebra using polyaxial orthopedic bone screws. The modular device has two angled longitudinal connectors, a spacer, and a connecting screw. The longitudinal connectors capture the guide rod cranially, and are also fixed to polyaxial bone screws which are anchored into the pars/pedicles of the 2nd cervical vertebra. Once implanted, the device will limit translational motion of the vertebrae in relation to one another in all planes, but will allow for rotation of the C1 vertebrae in relation to the C2 vertebrae. The modular design and use of polyaxial screws for attachment accommodate variability in patient size.

The motion preservation device allows for significant rotation of the C1 vertebrae about the C2 dens compared to other orthopedic spine devices. A circumferential rod is used as a guide for restored axial rotation. A modular assembly of the stabilization mechanism allows for ease of implantation and adjustment. The device stabilizes the atlantoaxial junction to within physiological limits.

Embodiments of the invention are also related to an apparatus that includes a first leg having a first connection portion, a second leg having a second connection portion, and a curved guide rod slidable within the first and second connection portions.

In some embodiments, the first leg comprises a first elongated shaft extending from the first connection portion along a first axis at an angle with respect to a vertical axis. In some embodiments, the first connection portion comprises a first block that vertically extends from the first elongated shaft along the vertical axis, wherein the block defines an ovalized passage sized to allow passage of the curved guide rod.

In some embodiments, the second leg comprises an elongated shaft extending from the first connection portion along a second axis at an angle with respect to a vertical axis.

In some embodiments, the second connection portion comprises a second block that vertically extends from the second elongated shaft along the vertical axis, wherein the second block defines a second ovalized passage sized to allow passage of the curved guide rod.

In some embodiments, the curved guide rid is curved to mimic anatomic rotational motion of an average person.

In some embodiments, the first connection portion includes a through hole for free passage of a screw and wherein the second connection portion includes a threaded hole for threadably receiving the screw and a spacer therebetween.

Embodiments of the invention are also related to a method. In this method, a first leg having a first connection portion is fixedly attached to a first portion of a lower vertebrae. A second leg having a second connection portion is fixedly attached to a second portion of a lower vertebrae. A curved guide rod is arranged to be slidable within the first and second connection portions. A first lateral portion of the curved guide rod is fixedly attached to a first portion of an upper vertebrae. A second lateral portion of the curved guide rod is fixedly attached to a second portion of an upper vertebrae. After fixedly attaching the first leg, second leg, and curved guide rod, the upper vertebrae is free to rotate with respect to lower vertebrae by way of the curved guide rod sliding within the first and second connection portions while being vertically and horiztontally stabilized.

In some embodiments, the first and second connection portions of the first and second legs are fixedly attached to one another.

In some embodiments, a spacer separates the first and second connection portions.

In some embodiments, the first and second portions of the lower vertebrae comprise first and second lateral masses of the lower vertebrae.

In some embodiments, the first and second legs are secured to the lower vertebrae using screws.

In some embodiments, the first and second lateral portions of the curved guide rod are secured to the upper vertebrae using screws.

BRIEF DESCRIPTION OF THE DRAWINGS

FIG. 1A shows a view of the Longitudinal Connector (Leg)—Close Fit Hole, according to an embodiment of the invention.

FIG. 1B shows another view of the Longitudinal Connector (leg)—Close Fit Hole, according to an embodiment of the invention.

FIG, 1C shows yet another view of the Longitudinal Connector (Leg)—Close Fit Hole, according to an embodiment of the invention.

FIG. 1D shows still another view of the Longitudinal Connector (leg)—Close Fit Hole, according to an embodiment of the invention.

FIG. 2A shows a view of the Longitudinal Connector (Leg)—Tapped Hole, according to an embodiment of the invention.

FIG. 2B shows another view of the Longitudinal Connector (Leg)—Tapped Hole, according to an embodiment of the invention.

FIG. 2C shows yet another view of the Longitudinal Connector (Leg)—Tapped Hole, according to an embodiment of the invention.

FIG. 2D shows still another view of the longitudinal Connector (Leg)—Tapped Hole, according to an embodiment of the invention.

Figure 3C:
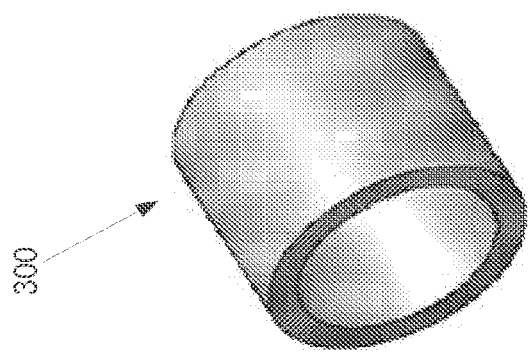
Figure 3B:
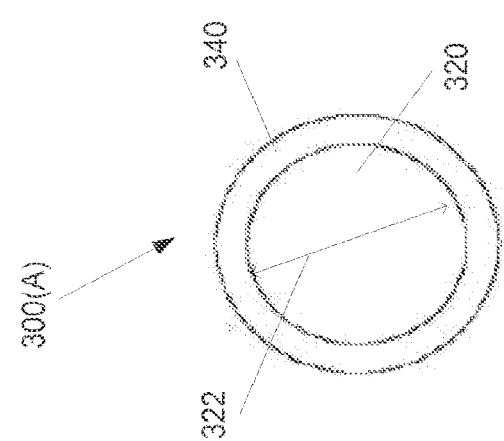
Figure 3A:
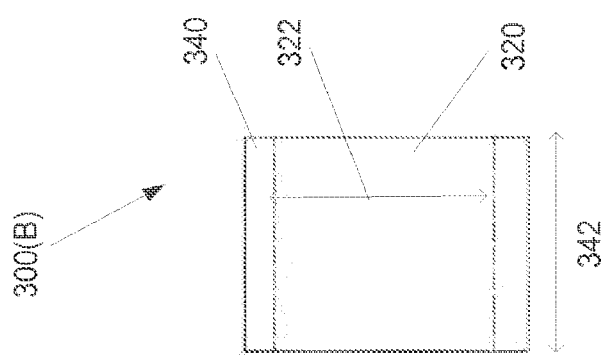

FIG. 3A shows a view of a spacer, according to an embodiment of the invention.

FIG, 3B shows another view of a spacer, according to an embodiment of the invention.

FIG, 3C shows yet another view of a spacer according to an embodiment of the invention.

FIG. 4A shows a view of an assembled implant, according to an embodiments of the invention.

FIG, 4B shows another view of an assembled implant, according to an embodiment of the invention.

FIG. 4C shows yet another view of an assembled implant, according to an embodiment of the invention.

FIG. 4D shows still another view of an assembled implant, according to an embodiment of the invention.

FIG. 5A shows an exploded view of the embodiment of FIGS. 4A. 4B, 4C and 4D.

FIG. 5B shows another exploded view of the embodiment of FIGS. 4A, 4B, 4C and 4D.

Figure 6:
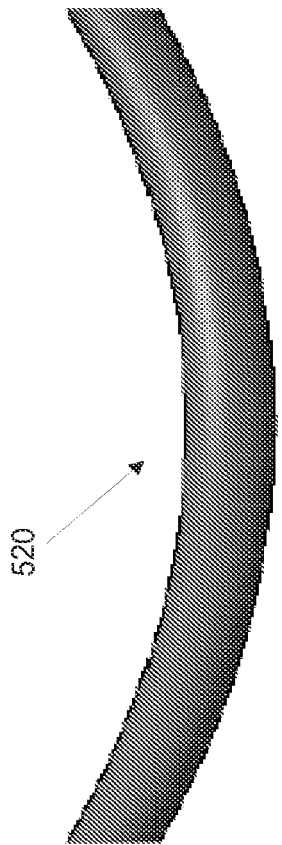

FIG. 6 shows the curved guide rod, according to some embodiments of the invention.

FIG. 7 illustrates a cut view of the device exposing the oval hole and screw hole, according to some embodiments of the invention.

FIG. 8A shows a view of the embodiment of FIGS. 4A, 4B, 4C, and 4D implanted within the spine—not including polyaxial pedicle screws to hold it in place, according an embodiment of the invention.

FIG. 8B shows another view of the embodiment of FIGS. 4A, 4B, 4C, and 4D implanted within the spine—not including polyaxial pedicle screws to hold it in place, according an embodiment of the invention.

FIG.8C shows yet another view of the embodiment of FIGS. 4A, 4B, 4C, and 4D implanted within the spine—not including polyaxial pedicle screws to hold it in place, according an embodiment of the invention.

DETAILED DESCRIPTION OF THE INVENTION

Referring now to the invention in more detail, FIG. 4 shows multiple perspective views of an assembled device 400 including a device base structure with additional attaching components for implantation. The device base structure is shown in more detail in FIG. 5, showing multiple exploded views of the device base structure 500 that includes five main components. The device base structure 500 is comprised of a longitudinal connector (e.g., a first leg) 100 with a close fit hole 140 (shown in detail in FIG. 1), a second leg 200 with a tapped hole 240 (shown in detail in FIG. 2), a spacer 300 (shown in detail in FIG. 3), a curved guide rod 520 (shown in detail in FIG. 6) and a connecting screw 450. 500(A) shows another perspective exploded view of the device base structure 500, including the first 100, the second leg 200, the spacer 300, the curved guide rod 520, and the connecting screw 450 to connect the first leg 100 to the second leg 200 with the spacer 300 in between to create a fixed spacing between the first leg 100 and the second leg 200.

The connecting screw 450 may be a standard screw threaded with a fixed thread pitch, or any other suitable screw to connect the first leg 100 with the second leg 200 spaced apart by the spacer 300. Each of the main components of the device base structure 500 will be described in more detail below with respect to their corresponding figures.

Referring to FIG. 1 showing the first leg 100 and FIG. 2 showing the second leg, multiple perspective views are shown. The two legs FIG. 1 and FIG. 2 are designed with two features. The first feature shows the bottom of the leg starting as a shaft and the second feature is the top block which has an oval hole and a second hole. In FIG. 1, the first leg 100 includes a shaft 160 and a top block 180 including a first hole 120 and a second hole 140. The top block 180 of the first leg can serve as a first connection portion of the first leg 100. The shaft 160 of the first leg may be elongated and extend from the top block 180 at an angle with respect to a vertical axis, the vertical axis being in line with the top block 180 of the first leg, as shown in the side view perspective 100(B). The top block 180 can extend vertically from the shaft 160 along the vertical axis.

The first hole 120 can be an oval hole and may be configured to allow slidable passage of a curved guide rod. The second hole 140 can be a close fit hole to allow for free passage of a connecting screw 450. The first leg 100(A) shows a front perspective view of the first leg 100. A side perspective view of the first leg 100 is shown in 100(B), and a top perspective view is shown in 100(C). The oval hole 120 (e.g., first hole, oval passage) can include a vertical diameter and a horizontal diameter, with a specific ratio between the vertical diameter and the horizontal diameter, to accommodate a thickness and shape of the curved guide rod 520 (of FIGS. 4 and 5). The close fit hole 140 (e.g., second hole) can include a fixed diameter to accommodate free passage of the connecting screw 450 (of FIGS. 4 and 5).

In FIG. 2, the second leg 200 can include a shaft 260 and a top block 280 having a tapped hole 240 and an oval hole 220. As in the first leg 100, the top block 280 of the second leg 200 can serve as a second connection portion of the second leg. The shaft 260 of the second leg may be elongated and extend from the top block 280 at an angle with respect to a vertical axis, the vertical axis being in line with the top block 280 of the second leg, as shown in the side view perspective 200(B). The top block 280 can extend vertically from the shaft 260 along the vertical axis.

The tapped hole 240 of the second leg 200 in FIG. 2 allows for placement of the connecting screw 450 (of FIGS. 4 and 5). The tapped hole 240 can be threaded with a pitch corresponding to the thread pitch of the connecting screw 450 (of FIGS. 4 and 5), thus configured to threadably receive the connecting screw 450 with a spacer 300 in between the first leg 100 and the second leg 200. Similar to the first leg 100, the oval hole 220 of the second leg 200 can include a vertical diameter and a horizontal diameter, with a specific ratio between the vertical diameter and the horizontal diameter, to accommodate a thickness and shape of the curved guide rod 520 (of FIGS. 4 and 5). The oval hole 220 of the second leg 200 can be angled to provide slidable passage of the curved guide rod 520. A front perspective view of the second leg 200 is shown in 200(A). A side perspective view of the second leg 200 is shown in 200(B), and a top perspective view is shown in 200(C).

The spacer 300 is shown in FIG. 3. A front perspective view of the spacer 300 is shown in 300(A), including an opening 320 with a diameter 322. 300(B) shows a side perspective view of the spacer 300. The spacer 300 can have a thickness 340 and a width 342, the width 342 being the distance the spacer 300 can maintain between the first leg 100 and the second leg 200. The width of the spacer 300 can be altered and customized depending on the size of the spinous process of a patient.

FIG. 6 shows an example of the curved guide rod 520. The curved guide rod can have a slightly larger width than height, thereby creating an oval cross-section, and can be slidable through the oval hole 120 of the first leg 100 and the oval hole 220 of the second leg 200. The curved guide rod 520 can have a radius of curvature. The radius of curvature for the guide rod 520 can be determined based on measurements of the patient and/or configured to mimic the anatomic rotational motion of the average person (e.g., radius of curvature can be 36.25 mm, based off the measurements of 8 human anatomical specimens). The curved guide rod 520 can be implanted and held fixed in place with the polyaxial screws 422, 424 (of FIG. 4) placed in the lateral masses of C1 (shown in FIG. 8) to fixedly attach the device 400. The approximate location of the device and rod placement are shown in FIG. 8, and can be determined based on measurements of the patient.

Referring to FIG. 7, the assembly of the device base structure 500 of FIG. 5 can be shown. 700(A) shows a cross section at line axis A of 700, which shows a top perspective view of the device base structure 500 without the curved guide rod 520. In the cross section 700(a), the first leg 100 and the second leg 200 are joined by connecting screw 450 and spaced apart by spacer 300, thus the legs 100 and 200 are fixedly attached to one another via the connecting screw 450 and spacer 300. The shafts 160 and 260 are at an angle can be fixed or customized depending on the size of the spinous process of the patient and placement on the patient. A length of the shafts 160, 260 can also be fixed or in other embodiments, customized depending on the patient. The connecting screw 450 joins the first leg 100 and the second leg 200 through the close fit hole 140 of the first leg 100 and the tapped hole 240 of the second leg 200 with the spacer 300 in between. Thus, the oval hole 120 of the first leg 100 and the oval hole 220 of the second leg 220 can be parallel and also spaced by the width 342 of the spacer 300.

The curved guide rod 520 may then be passed through the oval holes 120 220, the oval holes 120 and 220 providing slidable passage for the curved guide rod 520. The curved guide rod 520 may be arranged to be slidable between the top portions 180, 280 of the first leg 100 and the second leg 200, respectively, such that it is rotatable within the oval holes 120, 220 of the legs 100, 200, thus when fixedly attached to the lateral masses C1 and C2, allows the upper vertebrae to rotate freely with respect to the lower vertebrae while being vertically and horizontally stabilized.

FIG. 4 shows multiple exemplary views of an assembled device 400, including the device base structure 500 of FIG. 5 with polyaxial screws. A polyaxial screw can be used for connecting vertebrae to rods in spinal surgery. The legs 100, 200 start with cylindrical shafts 160, 260 which can fit into market-approved and clinically used polyaxial screws 420, and 426. Polyaxial screws 420 and 426 can be placed in the lateral masses of C2 (shown in FIG. 8). The shafts 160, 260 of the legs 100, 200 can fasten to the polyaxial screws 420 and 426 via locking caps 434 and 436. Polyaxial screws can have a spherical head or locking cap, enclosed in a housing, which allows the screw a range of motion along several different axis relative to the housing. A ball joint internal to the housing allows flexibility in placing the screws.

The top blocks 180, 280 of the legs 100, 200 can be connected via the curved guide rod 520 and attached to polyaxial screws 422, 424 via locking caps 430, 432. The locking caps 430 and 432 can include a housing 432(a) to allow for the polyaxial screws 422 and 424 to engage into the lateral masses C1 during implanting and can also be configured to enclose the curved guide rod 520. The locking caps 434 and 436 may be configured to allow the polyaxial screws 420 and 426 to engage into the lateral masses C2 during implanting of the device 400.

A diameter of the shaft 160, 260 can be determined based on a level of stability created when the device encounters loading stresses and a size of the polyaxial screw heads for proper fitting. Assembled device 400 is shown from a top perspective view in 400(A). A side perspective view from the side of the first leg 100 of the assembled device 400 is shown in 400(B). A front perspective view of the assembled device 400 when implanted is shown in 400(C).

The oval holes 120 and 220 on the top blocks 180, 280 of the legs 100, 200 (e.g., longitudinal connectors) can serve to fit the curved guide rod 520 as the assembled device 400 undergoes normal head and neck motions when surgically implanted (as shown in FIG. 8). The oval holes 120 and 220 can be sized according to the diameter, thickness, and cross-sectional shape of the curved guide rod 520. The oval shape allows for slidable passage of the curved guide rod 520 to follow a smooth rotation and can feature a slightly larger horizontal diameter (e.g., width) than vertical diameter (e.g., height).

The close fit hole 140 of the first leg 100 and tapped hole 240 of the second leg 200 can be secondary holes in the top block portions 180, 280 of the legs 100, 200. The secondary holes 140, 240 can be utilized with the connecting screw 450 and spacer 300, allowing the device 400 to be modular. The width of the device 400 can be altered depending on the size of the spinous process of the patient by using different sized spacers 300, and/or angle of the shafts 160, 260 of the legs 100, 200. The tapped hole 240 of the second leg 200 may allow the connecting screw 450 to tighten, holding the two legs 100, 200 and the spacer 300 together.

As shown in FIG. 8, the assembled device 400, in conjunction with the curved guide rod 520, provides a unique approach to stabilize the atlantoaxial junction, while still allowing rotational motion of C1 and C2. Translational motion is maintained within physiological limits in the anterior/posterior (AP) plane by fixing the shaft part of the legs to the lateral masses of C2 with polyaxial screws (e.g., pedicle screws). The curved guide rod 520 is also held fixed, via the polyaxial screws 422 and 424, to the lateral masses of C1. Combining the fixed shaft portions 160, 260 of the legs 100, 200 and the fixed curved guide rod 520 that runs through the oval holes 120, 220, C1 and C2 can move as a unit in AP motion, thus creating stability. In addition to reducing unnatural AP motion, the curved guide rod 520 and the oval holes 120, 220 of the two legs 100, 200 allow the device 400 to restore axial motion to the joint in a natural range of motion. The device 400 provides a means for stabilizing the atlantoaxial junction while allowing for axial rotation in cases of acquired ligamentous injury or fracture of the dens.

Surgical Technique

Placement of the device is effected via a standard posterior approach to the upper cervical spine. After induction of general anesthesia, cranial tongs are applied in a standard fashion and the patient is carefully positioned prone on bolsters. A midline posterior approach is used with exposure of the C2,3 facet joint and posterior elements. Similarly, a wide exposure of the C1 posterior arch and C1 lateral mass is performed. Hemostasis is secured and maintained with the use of hemostatic materials and bipolar cautery per surgeon preference.

After exposure of the posterior elements, screws are inserted in the C2 pars with a start point on the dorsal inferior aspect of the C2 inferior facet. A midsagittal trajectory is used for AP positioning and palpation and visualization of the medial and superior cortical aspects of the C2 pars may aid in screw orientation. Lateral fluoroscopic images assist positioning of the C2 screw in the midsubstance of the pars on the lateral projection.

Similarly, after exposure of the C1 lateral mass, the C1 screw is positioned by drilling in an anatomic direction, generally straight ahead in the AP plane or with slight medial inclination. Unicortical drilling is typically recommended and the longest screw path possible without perforating the anterior cortex of C1 is desirable to maximize fixation in C1.

Screw lengths for the C1 screw range between 34 and 40 mm, while C2 screw lengths between 16 and 20 mm may be employed depending on the vertebral artery anatomy and patient size. 3.5-4.0 mm diameter screws are available and may be placed per surgeon discretion.

Screw heads are oriented to accept the angled connectors from the caudal ends of the C1-2 longitudinal connectors. Assembly of the device is completed by selecting an appropriate length spacer and connecting the screw to fasten together the left and right longitudinal connectors. The curved rod is seated in the polyaxial screw head affixed to C1 only after it is threaded though the opening in the cranial end of the longitudinal connectors. All locking caps are torqued to manufacturers' specifications after fine adjustment of the C1-2 device is completed. Intraoperative imaging is recommended to verify accurate reduction of the atlantoaxial joint prior to device placement and to ensure appropriate screw placement prior to installation of the motion preserving device.

The wound is then closed in layers. Perioperative antibiotic prophylaxis is recommended. Postoperative immobilization with a cervical orthosis is also recommended for a period of six weeks to allow soft tissue healing. Postoperative plain radiographs should be obtained to verify accurate device placement. Interval radiographs postoperatively are recommended at 1, 3, 6, 12 and 24 months to ensure maintenance of reduction.

While the exemplary embodiments have been described in some detail for clarity of understanding and by way of example, a number of modifications, changes, and adaptations may be implemented. Further, any dimensions mentioned are exemplary guidelines for one skilled in the art, and thus do not necessarily represent limitations as to size and/or proportion of embodiments of the invention.

What is claimed is:

1. An apparatus comprising:
   a first leg having a first connection portion, wherein the first leg comprises a first elongated shaft extending from the first connection portion along a first axis at an angle with respect to a vertical axis and wherein the first connection portion includes a through hole for free passage of a screw;
   a second leg having a second connection portion wherein the second leg comprises a second elongated shaft extending from the second connection portion along a second axis at an angle with respect to a vertical axis and wherein the second connection portion includes a threaded hole for threadably receiving the screw and a spacer therebetween; and
   a curved guide rod slidable within the first and second connection portions.

2. The apparatus of claim 1, wherein the first connection portion comprises a first block that vertically extends from the first elongated shaft along the vertical axis, wherein the block defines an ovalized passage sized to allow passage of the curved guide rod.

3. The apparatus of claim 1 claim wherein the second connection portion comprises a second block that vertically extends from the second elongated shaft along the vertical axis, wherein the second block defines a second ovalized passage sized to allow passage of the curved guide rod.

4. The apparatus of claim 3, comprising polyaxial screws to respectively attach the first block and the second block to vertebrae.

5. The apparatus of claim 1, wherein the curved guide rod is curved to mimic anatomic rotational motion of an average person.

6. The apparatus of claim 1, wherein the curved guide rod is to limit translational motion and allow axial rotation of particular vertebrae.

7. The apparatus of claim 1, wherein the curved guide rod comprises a guide for axial rotation of particular vertebrae.

8. The apparatus of claim 1, comprising polyaxial screws to connect vertebrae respectively to the first and second connection portions.

* * * * *